United States Patent [19]

Drake

[11] Patent Number: 4,482,757

[45] Date of Patent: Nov. 13, 1984

[54] CLEAVAGE OF HYDROPEROXIDES

[75] Inventor: Charles A. Drake, Bartlesville, Okla.

[73] Assignee: Phillips Petroleum Company, Bartlesville, Okla.

[21] Appl. No.: 507,399

[22] Filed: Jun. 24, 1983

[51] Int. Cl.³ .............................................. C07C 37/08
[52] U.S. Cl. ...................................... 568/798; 568/385
[58] Field of Search ................ 568/798, 768, 741, 385

[56] References Cited

U.S. PATENT DOCUMENTS

| | | | |
|---|---|---|---|
| 2,663,735 | 12/1953 | Filar et al. | 568/798 |
| 2,683,751 | 7/1954 | Filar | 568/798 |
| 2,737,527 | 3/1956 | Mosaler | 568/798 |
| 2,748,172 | 5/1956 | Rodgers | 568/798 |
| 2,889,368 | 6/1959 | Hiratsuka et al. | 568/798 |
| 2,993,074 | 7/1961 | Shepard | 568/798 |
| 3,497,561 | 2/1970 | Gelbein | 568/798 |
| 3,959,381 | 5/1976 | Arkell et al. | 568/798 |
| 4,209,465 | 6/1980 | Austin et al. | 568/798 |

*Primary Examiner*—Werren B. Lone

[57] ABSTRACT

Secondary alkyl-substituted benzene hydroperoxides are cleaved to phenols and ketones by contacting the hydroperoxide with a mixture consisting essentially of an organic phosphonium halide compound and an acid at a temperature from about 0°–200° C.

10 Claims, No Drawings

CLEAVAGE OF HYDROPEROXIDES

This invention relates to the cleavage of hydroperoxides.

The use of aqueous acid catalyst systems such as $H_2SO_4$ and water for the cleavage of hydroperoxides to phenols and ketones is well known in the art. While such a catalyst system is operable for its intended use, it is not without disadvantages.

An aqueous acid catalyst system tends to make product separation (i.e. phenols and ketones) difficult because a neutralization step is frequently required. Furthermore, the use of aqueous acid systems sometimes results in the formation of azeotropes such that the products cannot be separated by either simple or fractional distillation. Therefore, a catalyst system which gives good yields and selectivities to phenols and ketones from the cleavage of hydroperoxides but avoids the problems mentioned bove is highly desirable.

It is therefore an object of this invention to provide an improved process for the cleavage of hydroperoxides to phenols and ketones.

Other aspects, objects, and advantages of the present invention are apparent from the specification and claims.

In accordance with the present invention, I have discovered that secondary-alkyl substituted benzene hydroperoxides are effectively cleaved by contacting the hydroperoxide with a mixture consisting essentially of (a) an organic phosphonium halide compound of the general formula $R'''_4PX$, wherein $R'''$ is a $C_1$ to $C_{20}$ aryl, alkyl, alkaryl, or aralkyl radical, and X is a halogen, and (b) at least one acid selected from the group consisting of an inorganic mineral acid or a carboxylic acid of the formula $R^{IV}COOH$ wherein $R^{IV}$ is a $C_1$ to $C_5$ alkyl group. By utilizing such a catalyst system relatively short reaction times, moderate reaction temperatures, and easy product separation are accomplished.

The secondary-alkyl substituted benzene hydroperoxides contemplated for use in the present invention are represented by the general formula:

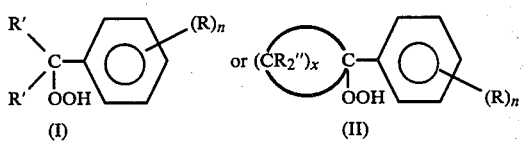

wherein R is a $C_1$–$C_{20}$ alkyl, cycloalkyl, or alkaryl radical, R' is independently a $C_1$ to $C_{10}$ alkyl, aryl, or alkaryl radical, R" is independently H or a $C_1$ to $C_{10}$ alkyl, aryl, or alkaryl radical, n is an integer from 0–5, and x is an integer from 2 to 11. Exemplary compounds falling under formulae (I) or (II) suitable for use in the present invention include cyclohexylbenzene hydroperoxide, cumene hydroperoxide, sec-butylbenzene hydroperoxide, sec-pentylbenzene hydroperoxide, and sec-hexylbenzene hydroperoxide with cyclohexylbenzene hydroperoxide being preferred.

Examples of suitable organic phosphonium halide compounds contemplated for use in the present invention include benzyltriphenylphosphonium chloride, benzyltrimethylphosphonium chloride, benzyltriphenylphosphonium bromide, benzyltriphenylphosphonium iodide and mixtures thereof. Preferred is benzyltriphenylphosphonium chloride.

Such organic phosphonium halide compounds are available commercially, for example from Alfa Products, Thiokol/Ventron Division, Danvers, Mass.

In the present invention, it is contemplated that any inorganic mineral acid may be used, preferably a non-oxidizing acid such as $H_2SO_4$, HCl, or $H_3PO_4$, and mixtures thereof. Preferred is $H_2SO_4$.

Carboxylic acids of the general formula $R'''COOH$ contemplated for use in the present invention include acetic, propionic, butyric, and mixtures thereof.

The following Table discloses both broad and preferred ranges contemplated for use in the present invention for the above additives based upon wt % of the secondary-alkyl substituted benzene hydroperoxide.

TABLE

| Compound | Ranges Broad | Preferred |
|---|---|---|
| $R''_4PX$ | 0.1–5% | 0.5–2% |
| Acid | 0.1–10% | 1–3% |

In the present invention the compounds of formulae (I) or (II) are decomposed to phenols and ketones. For example, cyclohexylbenzene hydroperioxide is decomposed to phenol and cyclohexanone.

The process of the present invention is carried out by contacting the secondary-alkyl substituted benzene hydroperoxide with a mixture of an organic phosphonium halide compound and an acid at a temperature in the broad range of from about 0°–200° C., with 40°–100° C. preferred.

The decomposition process can be carried out either batch-wise or continuously, using a hot tube reactor, stirred batch reactor, or other suitable contacting techniques.

Generally, the reaction time will be from about 5 minutes to 5 hours., preferably from about 30 to 120 minutes.

While the pressure at which the process of the present invention is carried out is not believed to be critical, it is broadly from sub-atmospheric to about 1000 psig with about atmospheric to 50 psig preferred.

The reaction products may be isolated by conventional procedures such as distillation and extraction. The residual products, can, if desired, be purified by conventional procedures such as column chromatography or fractional recrystallization.

The following examples illustrate the present invention.

EXAMPLE I

Preparation of Cyclohexylbenzene hydroperoxide

The cyclohexylbenzene hydroperoxide (CHBHP) feed employed in the following cleavage reaction was pooled from numerous laboratory investigations on the oxidation of cyclohexylbenzene (CHB), such as the following exemplary preparations. The pooled feed had a CHBHP concentration of 8.7 wt % in unreacted cyclohexylbenzene.

(a) Atmospheric oxidation of CHB:

A 300 mL 3-neck round bottom flask equipped with a dispersion tube and a magnetic stirrer was charged with 199 g of CHB and 1 g of cumene hydroperoxide. The flask was heated to 130° C. and $O_2$ introduced via the dispersion tube at about 0.8 standard cubic feed per hour (SCFH). Reaction was carried out for four hours at 130° C. and atmospheric pressure, then reactor contents sampled and analyzed by gas liquid chromatography (glc) using an internal standard. Typical CHB conversions of about 28% with selectivity to CHBHP of about 70% were obtained.

(b) CHB oxidation under pressure:

A 300 mL stainless steel Autoclave Engineers Magnedrive stirred tank reactor was charged with 49 g of cyclohexylbenzene and 1 g of cumene hydroperoxide. The reactor was then sealed, pressurized with $O_2$ to about 180 psig, and heated to about 120° C. for four hours. Typical CHB conversions of about 17% with selectivity to CHBHP to about 74% were obtained.

This example describes the typical preparations of the cyclohexylbenzene hydroperoxide employed in the following cleavage runs.

EXAMPLE II

General Reaction Procedure

All cyclohexylbenzene hydroperoxide cleavage reactions were carried out in a 100 mL round bottom flask equipped with a magnetic stir bar. Generally, about 14 g of crude oxidation product (see Example I), 0.4 g of internal standard (n-pentylbenzene), 0.05-0.5 g of catalyst and, optionally, about 10 mL of solvent were charged to the vessel. The reactor contents were stirred at room temperature to about 60° C. for about 30 minutes to about 2 hours, then sampled for analysis by gas liquid chromatography (glc). The product yields are corrected for the fact that only 90% of the hydroperoxide in the CHBHP feed is the correct hydroperoxide, i.e.

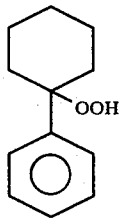

Other isomeric hydroperoxides are incapable of cleavage to give the desired ultimate products, phenol and cyclohexanone.

EXAMPLE III

CHBHP Cleavage

Several cleavage reactions were carried out according to the general procedure set forth in Example II. Catalyst employed (and amount), solvents employed (if any), reaction time and temperature, and product analysis are summarized in the Table.

of small amounts of $H_2SO_4$ (Run 4) is an active and selective catalyst system for the cleavage of cyclohexylbenzene hydroperoxide to given phenol and cyclohexanone. The results of Run 2 would suggest that substantially larger amounts of $H_2SO_4$ would have to be used to achieve results comparable to those obtained in Run 4.

Reasonable variations and modifications are possible from the foregoing disclosure without departing from the spirit and scope of the present invention.

I claim:

1. A process for the formation of ketones and phenols by the cleavage of a secondary alkyl substituted benzene hydroperoxide of the formula:

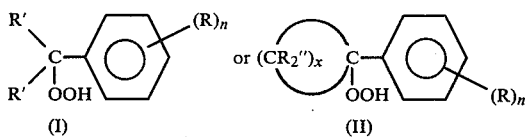

wherein R is a $C_1$–$C_{20}$ alkyl, cycloalkyl, or alkaryl radical, R' is independently a $C_1$ to $C_{10}$ alkyl, aryl, or alkaryl radical, R'' is independently H or a $C_1$ to $C_{10}$ alkyl, aryl, or alkaryl radical, n is an integer from 0–5, and x is an integer from 2 to 11;

comprising contacting said hydroperoxide with a mixture consisting essentially of (a) about 0.1–5 wt % based on the weight of said secondary-alkyl substituted benzene hydroperoxide of an organic phosphonium halide compound of the general formula $R'''_4PX$ wherein $R'''$ represents a $C_1$ to $C_{20}$ alkyl, aryl, alkaryl, or aralkyl radical and X is a halogen and (b) about 0.1–10 wt % based on said hydroperoxide of at least one acid selected from the group consisting of a mineral acid and a carboxylic acid of the formula $R^{IV}COOH$ wherein $R^{IV}$ is a $C_1$ to $C_5$ alkyl group at a temperature of from about 0°–200° C.

2. A process according to claim 1 wherein said secondary-alkyl substituted benzene hydroperoxide is cyclohexylbenzene hydroperoxide.

3. A process according to claim 1 wherein said organic phosphonium halide compound is benzyltriphenylphosphonium chloride.

4. A process according to claim 1 wherein said inorganic mineral acid is at least one selected from the group consisting of $H_2SO_4$, $H_3PO_4$, and HCl.

5. A process according to claim 4 wherein said inorganic mineral acid is $H_2SO_4$.

6. A process according to claim 1 wherein $C_1$ to $C_5$ carboxylic acid is at least one selected from the group consisting of acetic acid and propionic acid.

7. A process according to claim 1 wherein said or-

TABLE

| Run | Catalyst, g | CHBHP Chgd, g | Solvent, mL | Reaction Temp °C. | Reaction Time min | Yield Phenol | Yield % Cyclohexanone |
|---|---|---|---|---|---|---|---|
| 1 | $BF_3.H_3PO_4$, 0.05 | 14.3 | Acetone, 10 | 25 | 60 | 45 | 45 |
|   |   |   |   |   | 120 | 57 | 59 |
| 2 | 70% $H_2SO_4$, 0.5 | 14.2 | None | 60 | 30 | 24 | 12 |
|   |   |   |   |   | 60 | 36 | 18 |
| 3 | BTPC*, 0.1 | 14.2 | None | 60 | 60 | 0 | 0 |
| 4 | 70% $H_2SO_4$, 0.5 + BTPC, 0.1 | 14.2 | None | 60 | 30 | 90 | 65 |
|   |   |   |   |   | 60 | 94 | 78 |
|   |   |   |   |   | 90 | 99 | 89 |

*BTPC = benzyltriphenylphosphonium chloride

The results of these experiments demonstrate that benzyltriphenylphosphonium chloride in the presence ganic phosphonium halide compound is present in an amount of from 0.5–2 wt % based on the weight of said secondary-alkyl substituted benzene hydroperoxide.

8. A process according to claim 1 wherein said acid is present in an amount of from 1–3 wt % based on the weight of said secondary-alkyl substituted benzene hydroperoxide.

9. A process according to claim 1 wherein said temperature is from about 40° C. to about 100° C.

10. A process according to claim 1 wherein cyclohexylbenzene hydroperoxide, benzyltriphenylphosphonium chloride, and $H_2SO_4$ are present.

* * * * *